United States Patent
Charra et al.

(10) Patent No.: US 12,168,213 B2
(45) Date of Patent: Dec. 17, 2024

(54) ETHYLENE OLIGOMERIZATION PLANT FOR PRODUCING ALPHA-OLEFINS

(71) Applicant: IFP Energies nouvelles, Rueil-Malmaison (FR)

(72) Inventors: Cyprien Charra, Rueil-Malmaison (FR); Olivier Cotte, Rueil-Malmaison (FR); Frédéric Favre, Rueil-Malmaison (FR); Slavik Kasztelan, Rueil-Malmaison (FR); Jérôme Pigourier, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 207 days.

(21) Appl. No.: 17/912,088

(22) PCT Filed: Mar. 12, 2021

(86) PCT No.: PCT/EP2021/056417
§ 371 (c)(1),
(2) Date: Sep. 16, 2022

(87) PCT Pub. No.: WO2021/185706
PCT Pub. Date: Sep. 23, 2021

(65) Prior Publication Data
US 2023/0158471 A1    May 25, 2023

(30) Foreign Application Priority Data

Mar. 19, 2020 (FR) ................................. 2002708

(51) Int. Cl.
*B01J 19/30*  (2006.01)
*B01D 3/14*  (2006.01)
(Continued)

(52) U.S. Cl.
CPC .............. *B01J 19/30* (2013.01); *B01D 3/143* (2013.01); *B01J 10/00* (2013.01); *B01J 19/0013* (2013.01);
(Continued)

(58) Field of Classification Search
CPC ........ B01J 19/30; B01J 10/00; B01J 19/0013; B01J 19/2465; B01J 2219/00087;
(Continued)

(56) References Cited

U.S. PATENT DOCUMENTS 4,615,998 A    10/1986  Le Quan et al.
4,675,463 A *   6/1987  Glivicky ................. C07C 11/02
                                                          585/824

(Continued)

FOREIGN PATENT DOCUMENTS

EP    3338884 B1    7/2020

OTHER PUBLICATIONS

International search report PCT/EP2021/056417 dated May 20, 2021 (pp. 1-3) and English translation (pp. 1-2).

*Primary Examiner* — Ali Z Fadhel
(74) *Attorney, Agent, or Firm* — Millen, White, Zelano & Branigan, P.C.; Brion P. Heaney

(57) ABSTRACT

The present invention relates to a plant for oligomerizing ethylene to produce oligomerized alpha-olefins, with production of a fouling by-product in the form of a deposit, said plant comprising a reaction section comprising: —a reactor (c) for two-phase gas/liquid or single-phase all-liquid oligomerization proceeding from an optional solvent, an oligomerization catalyst and ethylene, and —cooling means associated with said reactor in the form of at least one cooling circuit external to the reactor and/or in the form of a jacket of the walls of the reactor. Packings are disposed in the reaction section in order to increase the contact surface (Continued)

area per unit volume that is accessible to the deposition of the byproduct.

21 Claims, 2 Drawing Sheets

(51) Int. Cl.
    *B01J 10/00*     (2006.01)
    *B01J 19/00*     (2006.01)
    *B01J 19/24*     (2006.01)
    *C07C 2/08*     (2006.01)

(52) U.S. Cl.
    CPC ............. *B01J 19/2465* (2013.01); *C07C 2/08* (2013.01); *B01J 2219/00087* (2013.01); *B01J 2219/00252* (2013.01)

(58) Field of Classification Search
    CPC .... B01J 2219/00252; B01J 2208/00212; B01J 2219/00094; B01J 2219/00247; B01D 3/143; C07C 2/08
    See application file for complete search history.

(56) References Cited

U.S. PATENT DOCUMENTS

| | | |
|---|---|---|
| 5,792,428 A | 8/1998 | Bakshi et al. |
| 6,004,256 A | 12/1999 | Townsend et al. |
| 6,274,783 B1 * | 8/2001 | Gildert ...................... C07C 2/12 585/533 |
| 7,511,183 B2 | 3/2009 | Blann et al. |
| 8,252,956 B2 | 8/2012 | Gao et al. |
| 8,816,147 B2 | 8/2014 | Vinel et al. |
| 9,931,622 B2 | 4/2018 | Magna et al. |
| 10,150,108 B2 | 12/2018 | Magna et al. |
| 10,370,307 B2 | 8/2019 | Boutrot et al. |
| 10,646,860 B2 | 5/2020 | Breuil et al. |
| 2013/0158321 A1 | 6/2013 | Olivier-Bourbigou et al. |
| 2018/0318819 A1 | 11/2018 | Breuil et al. |
| 2021/0395178 A1 * | 12/2021 | Barias ................... B01J 8/0496 |
| 2021/0403398 A1 * | 12/2021 | Barias ................... B01D 3/009 |
| 2022/0127208 A1 * | 4/2022 | Barias ....................... C07C 2/26 |
| 2022/0185745 A1 * | 6/2022 | Koenigs ................... C07C 7/20 |

* cited by examiner

ETHYLENE OLIGOMERIZATION PLANT FOR PRODUCING ALPHA-OLEFINS

TECHNICAL FIELD

The invention relates to the field of oligomerization of C2 to C4 olefins. This oligomerization aims to produce higher olefins such as butenes, hexenes, octenes, nonenes and decenes, which are olefins used as petrochemical first intermediates. The invention is more particularly directed towards the oligomerization of ethylene to give linear alpha-olefins, such as 1-butene, 1-hexene or 1-octene, or a mixture of linear alpha-olefins from 1-decene to 1-dodecene.

The oligomerization reaction is usually performed in a homogeneous catalysis process, notably in the liquid phase. It is moreover highly exothermic, generally requiring external cooling via heat exchangers.

PRIOR ART

The invention first relates to the field of oligomerization processes using two-phase gas/liquid reactors, in general with an implementation of bubble columns. Due to the exothermic nature of the oligomerization reactions, bubble columns also generally comprise one or more recirculation loops that consist in withdrawing a liquid fraction, cooling it by means of one or more exchangers and reintroducing it into the reaction chamber. Said recirculation loop makes it possible to obtain a good homogeneity of the concentrations and to control the temperature throughout the reaction volume. The plant also generally comprises, downstream of the oligomerization reactor, one or more separating columns, for isolating the desired reaction products, and optionally for recycling the solvent and/or the unreacted ethylene. Plants of this type are described, for example, in patents EP-2 703 373 and EP-3 338 884.

The invention also relates to the field of oligomerization processes employing single-phase liquid reactors that are used in particular for carrying out more specifically a tetramerization of the ethylene to give a mixture of alpha-olefins of 1-hexene and 1-octene type, with the same type of recirculation loop equipped with heat exchanger(s), and the same type of separating columns downstream of the reactor: This oligomerization reaction is also exothermic and also requires cooling means.

Irrespective of whether technology of two-phase reactor type or single-phase reactor type is used, a problem common to this type of reaction is encountered: that this oligomerization reaction generates a solid, fouling by-product of polymeric nature, as is explained in particular in the publication by R. F. Rossouw, R. L. J. Coetzer and P. D. Pretorius "Simulation experiments for maximising the availability of a commercial octene production facility", Volume 26(1), pp. 53-77 (2010)—published by ORION. This by-product tends to be deposited on the walls of the reactor and all of the equipment associated therewith in the reaction section, and especially on the heat exchange surfaces, in particular on the tubes of the heat exchangers in the recirculation loops mentioned above. However, the fouling of these heat exchange surfaces, more so than the other walls of the reaction section, is problematic since it gradually reduces the efficiency of the heat exchangers as the reaction progresses and as the fouling deposits become thicker. This is why regular cleaning operations targeted at the heat exchangers must be carried out: production must then be halted and the exchangers cleaned, generally by passing a hot liquid over their surface which will dissolve the deposits and remove them. These production stoppages are detrimental to the profitability of the process.

Patent EP-3 338 884 proposes improving the way in which the exchangers are cleaned by splitting the cooling means into two for a given reactor, with two solvent recirculation loops each equipped with heat exchangers and operating an alternation: one of the loops is in operation while the other, not in operation, is cleaned, for example using a hot fluid circulating in the cooling loop to be cleaned which dissolves and removes the deposits on the exchangers. This technical solution has the great advantage of not requiring production to be halted during the cleaning of the exchangers, this cleaning needing to be done more frequently than for the rest of the reaction section. However, this switch-over between the two cooling loops at regular intervals constitutes a constraint for the performance of the process on an industrial scale.

Indeed, irrespective of the way in which the exchangers are cleaned, the fact remains that the cleaning has to be carried out with relatively high frequency, for example on the order of a few hours on the industrial scale, which is a significant constraint for the performance of the industrial process, and, ultimately, for its profitability.

The aim of the invention is therefore that of improving the oligomerization plant/process using a gas/liquid reactor or an all-liquid reactor. The invention seeks in particular to improve the productivity/profitability of the process, in particular by acting more effectively on the fouling deposits produced during the oligomerization reaction.

In the context of the present text, the term "reaction section" refers to the reactor(s) of gas/liquid type, with a single reactor or several reactors in series and/or in parallel, and also any associated equipment thereof, and notably, in the case of the oligomerization processes with which the invention is concerned: —the cooling loop(s) comprising one or more heat exchangers and associated with the/with each of the reactors for controlling the exothermicity of the reaction, —the means for introducing the catalyst into the reactor(s), for example in the form of an introduction loop, which may or may not be separate from the cooling loop, —the means external to the reactor for separating/neutralizing the catalyst.

In the context of the present text, the term "fractionation section" denotes the device(s) for separation, notably by distillation, arranged downstream of the reaction section, with a single device or a plurality of devices arranged in series and/or in parallel, which devices may be identical or different in their sizing or their design/operation.

In the context of the present text, the terms "upstream" and "downstream" are understood as a function of the general direction of flow of the reaction fluid in the production unit.

In the context of the present text, when the oligomerization of ethylene is specifically mentioned, for the sake of brevity, the oligomerization of all C2 to C4 olefins is also intended, thus also propylene and 2-butene or isobutene.

SUMMARY OF THE INVENTION

A first subject of the invention is a plant for oligomerizing C2-C4 olefins, especially ethylene, to produce alpha-olefins, with production of a fouling by-product in the form of deposits, said plant comprising a reaction section having:—a reactor (c) for two-phase gas/liquid or single-phase liquid oligomerization proceeding from an optional solvent, a homogeneous oligomerization catalyst and ethylene, and— cooling means associated with said reactor in the form of at least one cooling circuit external to the reactor and/or in the form of a jacket of the walls of the reactor. According to the invention, packings are disposed in the reaction section in order to increase the contact surface area per unit volume that is accessible to the deposition of the byproduct.

These packings make it possible to slow down the fouling of the cooling means, and therefore the frequency of cleaning them.

It should also be noted that the invention applies, mutatis mutandis, not only to the oligomerization of ethylene, but also of (C2 to C4) olefins, either proceeding from only one of these olefins (for example only ethylene) or from a mixture of at least two of these olefins (for example an ethylene+propylene mixture).

It should also be noted that the homogeneous oligomerization catalyst may include a plurality of components, as detailed below, and that it is also referred to without distinction as catalytic (oligomerization) system in the present text. A homogeneous catalyst is understood to mean the fact that the catalyst or catalytic system is in the same phase as the reactants and the products of the oligomerization reaction.

The invention has demonstrated that it is possible to use packings for a purpose other than their usual use, these being customarily used for increasing the contact surface area between two different phases, for example between a liquid and a gas. Here, it was not a matter of promoting the contact between the reactants or between a reactant and its catalyst, but rather of increasing, in the reactor, the surface area at which the fouling by-product may be deposited, so as to correspondingly reduce the amount, and hence the thickness, of the deposits of this by-product on the heat exchangers. In fact, with the invention, it was possible to very significantly reduce the frequency of cleaning operations of the cooling means, since the rate of fouling of the exchangers is thereby greatly slowed. The fouling of the cooling means is therefore shifted towards the reactor, which at the very least is an unconventional choice. In addition, the presence of these packings also did not complicate or disturb the operation of the reactor, and the production yield between two cleaning operations remained the same even though one might have feared that this would have caused problems, especially in all-liquid reactors which never make use of such packings.

Preferably, the amount by which the contact surface area per unit volume of the reaction section (which therefore includes the internal volume of the reactor and the associated recirculation loops) is increased by virtue of the presence of the packings in the reaction section is chosen to be at least 5 $m^2/m^3$, in particular at least 10 $m^2/m^3$, preferably between 10 and 500 $m^2/m^3$. It is therefore a large increase in surface area which is targeted in order to obtain a sufficient slowing of the fouling of the exchangers and hence a sufficiently large interval between the cleaning thereof.

The invention can be implemented according to various embodiments. The packings may thus be disposed only in the reactor, or, in addition or alternatively, in other zones of the reaction section. In the case where the cooling means are at least one cooling circuit external to the reactor, the packings may be disposed only in the reactor, or in the reactor and in the cooling circuit(s), or else be disposed only in the cooling circuit(s).

Preferably, the packings are disposed in the liquid-filled volume VI of the reactor, in particular in at least 5% of said volume VI, in particular at most 100% of said volume VI, preferably between 30 or 50 and 90% or between 70 and 90% of said volume VI. In the case of an all-liquid reactor, it is therefore possible to fill up to the entire available volume of the reactor, and in the case of a gas/liquid reactor the packings are confined to the submerged portion of the interior of the reactor, since it is here that the fouling deposits occur and it is of no use to provide them in the "headspace" of the reactor.

The invention proposes using any type of packing. In a limiting manner, they can be chosen from at least one of the following packings: structured packing, random packing, internals defining fins or another developed geometric shape. Their geometry can be highly variable, especially depending on the shape and size of the reactor.

According to one embodiment, the external cooling circuit comprises at least one recirculation loop for the liquid phase of the reactor, said loop incorporating one or more heat exchangers.

In this case, the external cooling circuit may comprise at least two separate recirculation loops each incorporating one or more heat exchangers, and which are operational in alternation.

The plant according to the invention may comprise a section for separating the reaction effluents resulting from the reaction section, downstream of the oligomerization reactor, said separation section comprising at least a first column for fractionating said effluents so as to obtain a (top) fraction containing the starting olefin(s), and at least one other (bottom) fraction: the reaction mixture resulting from the oligomerization performed in the reactor is thus separated, said mixture comprising the C2-C4 olefins (ethylene), solvent, an oligomerization catalyst, and oligomerization products, so as to obtain a top fraction containing the starting olefin(s) (ethylene in this case) and at least one bottom fraction. Any known separation means may be used to do this, such as a distillation column downstream of the reactor. The aim of this separation is to recover the unreacted starting C2-C4 olefin(s) (ethylene), in particular in order to reuse them.

In this case, the separation section may additionally comprise, downstream of the first fractionating column, at least a second fractionating column so as to obtain at least one fraction enriched in alpha-olefin oligomerization products and one fraction enriched in solvent. Any known separation means may be used to do this, such as another distillation column downstream of the preceding one. The aim of this separation is to recover, for reuse, the optional solvent: thus, there is separation of at least a portion of the bottom fraction resulting from the separation of the mixture into at least one top fraction enriched in oligomerization products and one bottom fraction enriched in solvent, or into at least one top fraction enriched in solvent and one bottom fraction enriched in oligomerization products (the latter case being notably when it is desired to separate the optional solvent from heavy products).

Advantageously, at least a portion of the fraction enriched in optional solvent, known as recycled optional solvent, resulting from the second separation may thus be recycled to form part of the liquid phase entering the oligomerization reactor, especially after optional compression (in the case, notably, where the oligomerization reactor operates at high pressure). This liquid fraction is essentially composed of solvent, but may also comprise traces of alpha-olefin(s) (ethylene), of reaction products or by-products, and/or of the catalyst soluble in liquid medium.

It should be noted that, depending on the type of fractionating scheme chosen in the fractionating section, to be adapted as a function of the desired products, the separation of the solvent may be performed in the second separation or in an $n^{th}$ separation, performed downstream of the reaction section, at the top of the column or at the bottom of the column; the terms "first" and "second" separation are thus not to be understood literally and are merely indicated to mean that one takes place downstream of the other, but not necessarily consecutively.

Advantageously, the plant according to the invention comprises a loop for recycling the starting olefin(s) from the separation section to the reaction section. It is thus possible to recycle at least a portion of the top fraction resulting from the first fractionating column mentioned above, this top fraction containing the starting C2-C4 olefin(s). This gaseous fraction is essentially composed of the C2-C4 olefin(s) in question (ethylene), but may also comprise traces of heavier products (desired alpha-olefin, or other alkenes and/or alkanes produced by the reaction) and/or traces of solvent and/or traces of other compounds present in the ethylene feedstock (traces of methane, of ethane, etc.).

The plant according to the invention may thus also comprise a loop for recycling the starting olefin(s) from the separation section to the reaction section.

A subject of the invention is also a process for oligomerizing ethylene to produce oligomerized alpha-olefins proceeding from an optional solvent, a catalyst, in a reaction section comprising: —a reactor (c) for two-phase gas/liquid or single-phase all-liquid oligomerization proceeding from a solvent, a homogeneous oligomerization catalyst and ethylene, and—cooling means associated with said reactor in the form of at least one cooling circuit external to the reactor and/or in the form of a jacket of the walls of the reactor, such that the contact surface area per unit volume of the reactor which is available for the deposition of the fouling by-product is increased by disposing packings in the reaction section. It thus advantageously employs the plant described above.

According to one embodiment, the external cooling circuit of the reactor comprises according to the invention at least two separate recirculation loops each incorporating one or more heat exchangers, which are operational in alternation: at least one of the loops is operational while the exchangers of the other loop(s) which are not operational are being cleaned, in particular with the aid of a fluid the temperature of which is greater than the dissolution temperature of the fouling by-product.

Preferably, the oligomerization in the reactor is performed at a pressure of between 0.1 and 10.0 MPa and at a temperature of between 30 and 200° C.

The invention will be described with the aid of non-limiting examples of the oligomerization process under consideration, illustrated by the figures listed below.

BRIEF DESCRIPTION OF THE DRAWINGS

FIGS. 1 to 6 are very schematic and notably represent the various components of the plant without necessarily being to scale or representing the relative spatial configuration of the components under consideration, and being confined to representing the most important components for the purposes of the invention, so as to facilitate the reading thereof. Thus, notably, the figures do not show the cooling loop external to the oligomerization reactor which is necessary for controlling the exothermicity of the reaction in the reactor, or the catalyst injection system, or the fluid introduction means, which are known per se in oligomerization plants. References that are identical from one figure to the next correspond to the same streams/devices.

Figure 1:
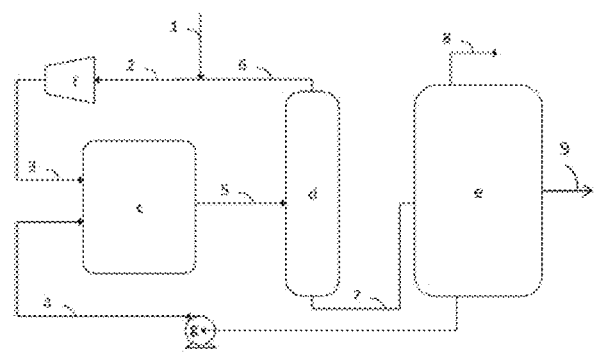
FIG. 1 represents a diagram of an ethylene oligomerization (tetramerization) plant capable of implementing the invention.

Moreover, it should be noted that the fractionation scheme may be more complex and may include more than two columns; it may also incorporate additional separating means other than columns, directed notably towards separating the spent catalyst from the reaction products and by-products, for instance flashes, thin-film evaporators or any other technology known to those skilled in the art. For more details, reference may be made, for example, to patent EP-3 338 884.

Definitions, Abbreviations and Conventions in the Context of the Present Invention The terms "upstream" and "downstream" should be understood as a function of the general flow of the fluid under consideration in the plant, from the introduction of the reagents, such as ethylene in this case, up to the recovery of the product of interest, namely the alpha-olefin(s) under consideration in the process.

The oligomerization corresponds to any reaction for the addition of a first olefin to a second olefin identical to or different from the first olefin. The olefin thus obtained has the empirical formula $C_nH_{2n}$, where n is equal to or greater than 4. The examples concern the main reaction of ethylene with itself to produce 1-butene and/or 1-hexene and/or higher oligomers. It includes the case of a tetramerization.

An alpha-olefin (in this case the product obtained after oligomerization) is a linear olefin in which the double bond is located in the terminal position of the alkyl chain.

In the examples, the homogeneous oligomerization catalyst is a mixture (also known as a catalytic system) of at least one metal precursor and of at least one activating agent, optionally in the presence of at least one additive and optionally of a solvent.

The liquid phase corresponds to the mixture of all of the compounds that are in a liquid physical state under the temperature and pressure conditions of the reaction section, including the entering fluid streams and the streams exiting towards the fractionating section.

The gaseous phase may correspond to the mixture of all of the compounds which are in a gaseous physical state under the temperature and pressure conditions of the reaction chamber (oligomerization reactor), which is in the form of bubbles present in the liquid phase, notably in the abovementioned entering streams, and also in single-phase form in the streams entering/exiting the reactor and optionally in the top part of the reactor (known as the "gaseous headspace" of the reactor).

As already seen, the oligomerization reaction section comprises the oligomerization reactor and its equipment, including at least one cooling loop, the means for introducing/removing the various fluids and the catalyst, in its simplest version. The invention also includes a reaction section composed of several oligomerization reactors, in series and/or in parallel. For the sake of brevity, the term "reactor" may rather be used when referring to the reaction section.

A "fresh" component (ethylene, solvent) is a component not recycled from a downstream step of the oligomerization process to a step further upstream or during the same step.

A "recycled" component, on the other hand, is a component produced, present in a downstream step of the process, separated and recycled to an upstream step. Recycled ethylene or solvent are to be considered as comprising, respectively, essentially ethylene and solvent, but being liable to comprise traces of other components.

For the sake of brevity, a detailed description will not be given hereinbelow of the entire oligomerization plant and of the operating conditions for its implementation which are not strictly linked to the invention: for further details regarding oligomerization as a whole, and for non-limiting examples of an oligomerization plant and process of interest to the invention, reference may be made notably to the abovementioned patents EP-2 703 373 and EP-3 338 884.

However, examples of reactant, solvent and catalyst and also the main modes of performing the oligomerization are given below: The oligomerization process according to the invention allows linear alpha-olefins to be obtained by placing in contact ethylene and a catalytic system, optionally in the presence of a solvent.

Any catalytic system known to a person skilled in the art and capable of being employed in the dimerization, trimerization or tetramerization processes and more generally in the oligomerization processes according to the invention falls within the field of the invention. Said catalytic systems and also the implementations thereof are notably described in patents FR 2 984 311, FR 2 552 079, FR 3 019 064, FR 3 023 183, FR 3 042 989 or else in patent FR 3 045 414.

It is recalled that:
the dimerization of ethylene makes it possible to obtain mainly butenes, in particular 1-butene, (generally without solvent)
the trimerization of ethylene makes it possible to obtain mainly hexenes, in particular 1-hexene,
the tetramerization of ethylene makes it possible to obtain mainly octenes, in particular 1-octene, (generally with solvent)

Preferably, the catalytic systems comprise, and preferably consist of:
a metal precursor, preferably based on nickel, on titanium or on chromium,
an activating agent or a mixture of activating agents,
optionally an additive, and
optionally a solvent.

The Metal Precursor

The metal precursor used in the catalytic system is chosen from compounds based on nickel, titanium or chromium.

In one embodiment, the metal precursor is based on nickel and preferentially comprises nickel in (+II) oxidation state. Preferably, the nickel precursor is chosen from nickel(II) carboxylates, for instance nickel 2-ethylhexanoate, nickel (II) phenates, nickel(II) naphthenates, nickel(II) acetate, nickel(II) trifluoroacetate, nickel(II) triflate, nickel(II) acetylacetonate, nickel(II) hexafluoroacetylacetonate, π-allylnickel(II) chloride, π-allylnickel(II) bromide, methallylnickel(II) chloride dimer, η3-allylnickel(II) hexafluorophosphate, η3-methallylnickel(II) hexafluorophosphate and nickel(II) 1,5-cyclooctadienyl, in their hydrated or non-hydrated form, taken alone or as a mixture.

In a second embodiment, the metal precursor is based on titanium and preferentially comprises a titanium aryloxy or alkoxy compound.

The titanium alkoxy compound advantageously corresponds to the general formula $[Ti(OR)_4]$ in which R is a linear or branched alkyl radical. Among the preferred alkoxy radicals, non-limiting examples which may be mentioned include tetraethoxy, tetraisopropoxy, tetra(n-butoxy) and tetra(2-ethylhexyloxy).

The titanium aryloxy compound advantageously corresponds to the general formula $[Ti(OR')_4]$ in which R' is an aryl radical which is unsubstituted or substituted with alkyl or aryl groups. The radical R' may include heteroatom-based substituents. The preferred aryloxy radicals are chosen from phenoxy, 2-methylphenoxy, 2,6-dimethylphenoxy, 2,4,6-trimethylphenoxy, 4-methylphenoxy, 2-phenylphenoxy, 2,6-diphenylphenoxy, 2,4,6-triphenylphenoxy, 4-phenylphenoxy, 2-(tert-butyl)-6-phenylphenoxy, 2,4-di(tert-butyl)-6-phenylphenoxy, 2,6-diisopropylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy, the biphenoxy radical, binaphthoxy and 1,8-naphthalenedioxy.

According to a third embodiment, the metal precursor is based on chromium and preferentially comprises a chromium(II) salt, a chromium(III) salt or a salt of different oxidation state which may include one or more identical or different anions, for instance halides, carboxylates, acetylacetonates or alkoxy or aryloxy anions. Preferably, the chromium-based precursor is chosen from $CrCl_3$, $CrCl_3(tetrahydrofuran)_3$, $Cr(acetylacetonate)_3$, $Cr(naphthenate)_3$, $Cr(2-ethylhexanoate)_3$ and $Cr(acetate)_3$.

The concentration of nickel, titanium or chromium is between 0.01 and 300.0 ppm by mass of atomic metal, relative to the reaction mass, preferably between 0.02 and 100.0 ppm, preferentially between 0.03 and 50.0 ppm, more preferentially between 0.5 and 20.0 ppm and even more preferentially between 2.0 and 50.0 ppm by mass of atomic metal, relative to the reaction mass.

The Activating Agent

Whatever the metal precursor, the catalytic system also comprises one or more activating agents chosen from aluminum-based compounds, such as methylaluminum dichloride ($MeAlCl_2$), dichloroethylaluminum ($EtAlCl_2$), ethylaluminum sesquichloride ($Et_3Al_2Cl_3$), chlorodiethylaluminum ($Et_2AlCl$), chlorodiisobutylaluminum (i-$Bu_2AlCl$), triethylaluminum ($AlEt_3$), tripropylaluminum ($Al(n-Pr)_3$), triisobutylaluminum ($Al(i-Bu)_3$), diethylethoxyaluminum ($Et_2AlOEt$), methylaluminoxane (MAO), ethylaluminoxane (EAO) and modified methylaluminoxanes (MMAO).

The Additive

Optionally, the catalytic system comprises one or more additives.

When the catalytic system is based on nickel, the additive is chosen from: compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or the compounds of phosphine type are independently chosen from tributylphosphine, triisopropylphosphine, tricyclopentylphosphine, tricyclohexylphosphine, triphenylphosphine, tris(o-tolyl)phosphine, bis(diphenylphosphino)ethane, trioctylphosphine oxide, triphenylphosphine oxide or triphenyl phosphite, or the compounds corresponding to the general formula (I) or a tautomer of said compound:

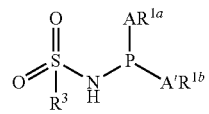

(I)

in which:

A and A', which may be identical or different, are independently an oxygen or a single bond between the phosphorus atom and a carbon atom, the groups $R^{1a}$ and $R^{1b}$ are independently chosen from methyl, trifluoromethyl, ethyl, n-propyl, isopropyl, n-butyl, isobutyl, t-butyl, pentyl, cyclohexyl and adamantyl groups, which may or may not be substituted and may or may not contain heteroelements; phenyl, o-tolyl, m-tolyl, p-tolyl, mesityl, 3,5-dimethylphenyl, 4-(n-butyl)phenyl, 2-methylphenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-bis(tert-butyl)-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups, the group $R^2$ is independently chosen from methyl, trifluoromethyl, ethyl, n-propyl, isopropyl, n-butyl, isobutyl, t-butyl, pentyl, cyclohexyl and adamantyl groups, which may or may not be substituted and may or may not contain heteroelements; phenyl, o-tolyl, m-tolyl, p-tolyl, mesityl, 3,5-dimethylphenyl, 4-(n-butyl)phenyl, 4-methoxyphenyl, 2-methoxyphenyl, 3-methoxyphenyl, 4-methoxyphenyl, 2-isopropoxyphenyl, 4-methoxy-3,5-dimethylphenyl, 3,5-di(tert-butyl)-4-methoxyphenyl, 4-chlorophenyl, 3,5-bis(trifluoromethyl)phenyl, benzyl, naphthyl, bisnaphthyl, pyridyl, bisphenyl, furanyl and thiophenyl groups.

When the catalytic system is based on titanium, the additive is chosen from diethyl ether, diisopropyl ether, dibutyl ether, diphenyl ether, 2-methoxy-2-methylpropane, 2-methoxy-2-methylbutane, 2,2-dimethoxypropane, 2,2-bis(2-ethylhexyloxy)propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-dioxane, dimethoxyethane, bis(2-methoxyethyl) ether, benzofuran, glyme and diglyme, taken alone or as a mixture.

When the catalytic system is based on chromium, the additive is chosen from:

compounds of nitrogenous type, such as trimethylamine, triethylamine, pyrrole, 2,5-dimethylpyrrole, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-trifluoromethylpyridine, 2-phenylpyridine, 3-phenylpyridine, 2-benzylpyridine, 3,5-dimethylpyridine, 2,6-di(tert-butyl)pyridine and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethylethane-1,2-diimine, N,N'-di(t-butyl)ethane-1,2-diimine, N,N'-di(t-butyl)butane-2,3-diimine, N,N'-diphenylethane-1,2-diimine, N,N'-bis(2,6-dimethylphenyl)ethane-1,2-diimine, N,N'-bis(2,6-diisopropylphenyl)ethane-1,2-diimine, N,N'-diphenylbutane-2,3-diimine, N,N'-bis(2,6-dimethylphenyl)butane-2,3-diimine or N,N'-bis(2,6-diisopropylphenyl)butane-2,3-diimine, or from aryloxy compounds of general formula $[M(R^3O)_{2-x}X_n]_y$, in which:

M is chosen from magnesium, calcium, strontium and barium, preferably magnesium, $R^3$ is an aryl radical containing from 6 to 30 carbon atoms and X is a halogen or an alkyl radical containing from 1 to 20 carbon atoms, n is an integer which can take the values of 0 or 1, and y is an integer between 1 and 10; preferably, y is equal to 1, 2, 3 or 4.

Preferably, the aryloxy radical $R^3O$ is chosen from 4-phenylphenoxy, 2-phenylphenoxy, 2,6-diphenylphenoxy, 2,4,6-triphenylphenoxy, 2,3,5,6-tetraphenylphenoxy, 2-(tert-butyl)-6-phenylphenoxy, 2,4-di(tert-butyl)-6-phenylphenoxy, 2,6-diisopropylphenoxy, 2,6-dimethylphenoxy, 2,6-di(tert-butyl)phenoxy, 4-methyl-2,6-di(tert-butyl)phenoxy, 2,6-dichloro-4-(tert-butyl)phenoxy and 2,6-dibromo-4-(tert-butyl)phenoxy. The two aryloxy radicals may be borne by the same molecule, for instance the biphenoxy radical, binaphthoxy or 1,8-naphthalenedioxy. Preferably, the aryloxy radical $R^3O$ is 2,6-diphenylphenoxy, 2-(tert-butyl)-6-phenylphenoxy or 2,4-di(tert-butyl)-6-phenylphenoxy.

or from the compounds having the general formula $(R^1)(R^2)X—Y—Z(R^3)(R^4)$, where X and Z are independently a phosphorus, arsenic, antimony, nitrogen or bismuth and Y is a group linking X and Z.

X and Z may independently be in the oxidized state bonded to an O, an N or an S.

Y may be selected from organic hydrocarbon and heterohydrocarbon linking groups or inorganic linkers, or ionic linkers, such as 1,2-ethane, 1,2-propane, 1,2-phenylene, —N($R^5$)—, —P($R^5$)—, —B($R^5$)—, —Si($R^5$)$_2$— where $R^5$ may be a hydrogen, a hydrocarbon group that is unsubstituted or substituted by a heteroatom or a halogen. Preferably, Y is a group of the —(N$R^5$)'— type, such as those described in the patents WO2004056477 and WO 2008119153.

An example of the type of catalytic system that can be used in the invention comprises: at least one chromium-based metal precursor, at least one heteroatomic ligand of general formula (I)

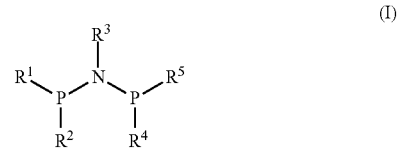

(I)

in which

R$^1$, R$^2$, R$^3$, R$^4$ and R$^5$, which may be identical to or different from one another, optionally bonded to one another, are chosen from a cyclic or noncyclic, aromatic or nonaromatic alkyl group having from 1 to 15 carbon atoms, optionally containing heteroelements.

Preferably, the R$^1$, R$^2$, R$^3$, R$^4$ and R$^5$ groups, which may be identical to or different from one another, optionally bonded to one another, are chosen from the methyl, ethyl, n-propyl, isopropyl, n-butyl, isobutyl, tert-butyl, pentyl, cyclopentyl, hexyl, cyclohexyl or adamantyl groups, which may or may not be substituted and may or may not contain heteroelements; the phenyl, o-tolyl, m-tolyl, p-tolyl, mesityl, 3,5-dimethylphenyl, 4-n-butylphenyl, 2-methoxyphenyl, 3-methoxyphenyl, 4-methoxyphenyl, 2-isopropylphenyl, 4-methoxy-3,5-dimethylphenyl, 3,5-di-tert-butyl-4-methoxyphenyl, 2-chlorophenyl, 3-chlorophenyl, 4-chlorophenyl, 2-fluorophenyl, 3-fluorophenyl, 4-fluorophenyl, 4-trifluoromethylphenyl, 3,5-di(trifluoromethyl)phenyl, benzyl, naphthyl, bisnaphthyl, pyridyl, furanyl or thiophenyl groups, which may or may not be substituted.

By way of nonlimiting example, mention may be made of the following heteroatomic ligands: (phenyl)$_2$PN(methyl)P(phenyl)$_2$, (phenyl)$_2$PN(isopropyl)P(phenyl)$_2$, (phenyl)$_2$PN(phenyl)P(phenyl)$_2$, (2-methoxyphenyl)$_2$PN(isopropyl)P(phenyl)$_2$, (2-methoxyphenyl)$_2$PN(isopropyl)P(2-methoxyphenyl)$_2$, (4-methoxyphenyl)$_2$PN(isopropyl)P(4-methoxyphenyl)$_2$, (2-fluorophenyl)$_2$PN(isopropyl)P(2-fluorophenyl)$_2$, (2-fluorophenyl)(phenyl)PN(isopropyl)P(2-fluorophenyl)$_2$, (2-fluorophenyl)(phenyl)PN(isopropyl)P(2-fluorophenyl)(phenyl), (2-fluorophenyl)(phenyl)PN(isopropyl)P(phenyl)$_2$, at least one activator chosen from aluminum-based compounds, such as methylaluminum dichloride (MeAlCl$_2$), dichloroethylaluminum (EtAlCl$_2$), ethylaluminum sesquichloride (Et$_3$Al$_2$Cl$_3$), chlorodiethylaluminum (Et$_2$AlCl), chlorodiisobutylaluminum (i-Bu$_2$AlCl), triethylaluminum (AlEt$_3$), trimethylaluminum (AlMe$_3$), tri-,-octylaluminum (AlOct$_3$), tripropylaluminum (Al(n-Pr)$_3$), triisobutylaluminum (Al(i-Bu)$_3$), diethylethoxyaluminum (Et$_2$AlOEt), methylaluminoxane (MAO), ethylaluminoxane (EAO) and modified methylaluminoxanes (MMAO).

The Solvent

In another embodiment according to the invention, the catalytic system itself optionally comprises one or more solvents. This or these solvent(s) may aid the introduction of the catalyst into the reaction section.

The solvent(s) are advantageously chosen from ethers, alcohols, halogenated (fluorinated, chlorinated, brominated or iodinated) solvents and aliphatic and cycloaliphatic hydrocarbons, comprising between 1 and 20 carbon atoms, preferably between 2 and 10 carbon atoms, preferably between 4 and 8, aromatic hydrocarbons comprising from 4 to 20 carbon atoms and preferably between 5 and 15 carbon atoms.

Preferably, the solvent is chosen from pentane, hexane, cyclohexane, methylcyclohexane, heptane, butane or isobutane, 1,5-cyclooctadiene, cyclopentadiene, benzene, toluene, ortho-xylene, mesitylene, ethylbenzene, diethyl ether, tetrahydrofuran, 1,4-dioxane, dichloromethane, chlorobenzene, methanol, ethanol, pure or as a mixture, and ionic liquids.

The solvent is chosen from the group formed by aliphatic and cycloaliphatic hydrocarbons, such as hexane, cyclohexane, heptane, butane or isobutane.

Preferably, the solvent used is cyclohexane.

In one embodiment, a solvent or a mixture of solvents may be used during the oligomerization reaction. Said solvent is advantageously chosen independently from the group formed by aliphatic and cycloaliphatic hydrocarbons, such as hexane, cyclohexane, heptane, butane or isobutane.

Preferably, the linear alpha-olefins obtained comprise from 4 to 20 carbon atoms, preferably from 4 to 18 carbon atoms, preferably from 4 to 10 carbon atoms and preferably from 4 to 8 carbon atoms. Preferably, the olefins are linear alpha-olefins chosen from but-1-ene, hex ene and oct-1-ene.

Advantageously, the oligomerization process is performed at a pressure of between 0.1 and 10.0 MPa, preferably between 0.2 and 9.0 MPa and preferentially between 0.3 and 8.0 MPa, at a temperature of between 30 and 200° C., preferably between 35 and 150° C. and in a preferred manner between 45 and 140° C.

Preferably, in the case of an oligomerization, the concentration of catalyst in the catalytic system is between 0.001 and 300.0 ppm by mass of atomic metal relative to the reaction mass, preferably between 0.02 and 100.0 ppm, preferably between 0.1 and 50.0 ppm, preferentially between 0.03 and 50.0 ppm, even more preferentially between 2.0 and 50.0 ppm, more preferentially between 0.5 and 20.0 ppm, or between 0.4 and 30.0 ppm, or between 0.6 and 20.0 ppm, for example between 0.8 and 10.0 ppm or between 1.0 and 6.0 ppm by mass of atomic metal relative to the reaction mass.

In the specific case of a tetramerization of ethylene, the concentration in question is between 0.001 and 1 ppm, in particular between 0.01 and 0.1 ppm.

According to one embodiment, the oligomerization process is performed batchwise. The catalytic system, constituted as described above, is introduced into the solvent inside a reactor equipped with the usual stirring, heating and cooling devices, then pressurization with ethylene is performed to the desired pressure, and the temperature is adjusted to the desired value. The oligomerization device is maintained at a constant pressure by introduction of gaseous ethylene until the total volume of liquid produced fills the desired fraction of the reaction volume. The catalyst is then neutralized by any usual means known to a person skilled in the art and the reaction products and the solvent are then withdrawn and separated.

According to another embodiment, the oligomerization process is performed continuously. The catalytic system, constituted as described above, is injected into a reactor stirred by conventional mechanical means known to a person skilled in the art or by external recirculation, and maintained at the desired temperature. The ethylene is also injected into the reactor via its own injection means. The components of the catalytic system can also be injected separately into the reaction medium and/or the solvent. The gaseous ethylene is generally introduced via a pressure-controlled intake valve, which keeps said pressure constant in the reactor or via an intake valve controlled by a flow-rate control. The reaction mixture is withdrawn by means of a liquid-level-controlled valve, so as to keep said level constant. The catalyst present in the withdrawn reaction mixture is neutralized continuously by any usual means known to a person skilled in the art and the products resulting from the reaction, and also the solvent, are then separated, for example by distillation. The ethylene which has not been converted can be recycled into the reactor. The catalyst residues included in a heavy fraction may be incinerated.

DESCRIPTION OF THE EMBODIMENTS

The examples and figures which follow concern, in a non-limiting manner, the oligomerization of ethylene.

A first embodiment relating to examples 1 to 4 concerns performing a tetramerization of the ethylene to obtain a mixture of 1-hexene and 1-octane, in a single-phase liquid reactor, with the plant of FIG. 1.

A second embodiment concerns performing an oligomerization of the ethylene to obtain 1-butene, 1-hexene or a collection of linear terminal olefins from 1-butene to 1-dodecene, in a two-phase liquid/gas reactor. It corresponds to examples 5 to 8 relating to the dimerization of ethylene, with the plant of FIG. 6.

Examples 1 to 4 described below thus correspond to a tetramerization of ethylene in a reactor comprising two external cooling loops operating in alternation, as described in particular in the above-mentioned patent EP-3 338 884.

As mentioned above, the invention applies mutatis mutandis to the oligomerization of other olefins such as propylene or butene, or a mixture of at least two thereof: the invention applies to C2 to C4 olefins, chosen from ethylene, propylene, 1-butene and 2-butene, isobutene, and preferably to ethylene.

FIG. 1 is a diagram of a plant implementing a process for oligomerization, of tetramerization type, of ethylene to which the invention can be applied: the main devices of the plant that the invention will affect are shown in a simplified manner, namely a liquid/gas oligomerization reactor, a first separation (distillation) column d and a second separation section comprising series distillation devices (columns) e, a pump g and a compressor f. The figure does not show the catalyst neutralization and separation section, which is well known per se, nor does it show the recirculation loops which are associated with the reactor c and which incorporate one or more heat exchangers.

The reactor c, which may be a series of reactors, and the distillation column d, and those included in the section e, define chambers which are for example oriented substantially along a vertical axis.

According to this diagram, and for purely illustrative purposes, the oligomerization reaction takes place in the reactor c at high pressure, between 20 and 90 bar absolute. The circulating streams are the following:

stream 1 is a stream of fresh ethylene stream 6 is a stream corresponding to the top fraction exiting the first column d, consisting essentially of ethylene (and of traces of compounds initially present in the fresh ethylene, and/or of solvent and of reaction products and by-products), which will be recycled stream 2 is the mixture of stream 1 of fresh ethylene and of stream 6 of recycled ethylene stream 3 is stream 2 once it has been compressed to the desired pressure by the compressor f, and which enters the reactor c as a gaseous phase stream 5 is the stream withdrawn from the reactor c after catalyst neutralization (neutralization not shown, performed on the stream exiting the reactor); this stream is therefore a mixture of solvent, neutralized catalyst, unreacted ethylene and reaction products stream 7 is the bottom fraction resulting from the separation performed in the first column d; it includes the solvent, the neutralized catalyst and the reaction products stream 8 is the stream of the reaction products separated in section e that are lighter than the solvent; the stream is therefore shown as exiting via the top of section e, stream 9 is the stream of the reaction products separated in section e that are heavier than the solvent; the stream is shown as exiting via the middle of section e, stream 4 is the stream of the solvent (and which may also contain traces of other compounds, notably of reaction products), which is separated in section e comprising the separation devices, which stream passes through a pump g and is then injected into an inlet of the reactor c as recycled liquid phase. Here, it is the heaviest stream, which is therefore shown as exiting the bottom of section e.

It should be noted, regarding the streams exiting the separation section e, that "top", "bottom", and "middle" are used for convenience, as if section e was just one distillation column in which the heaviest products exit at the bottom part of the column. It should also be noted that, if the solvent was heavier than the "heavy" reaction products and lighter than the "light" reaction products, stream 4 of solvent to be recycled would exit from section e via the middle, and the positions at which streams 4 and 9 exit from section e would thus be inverted.

The operation of such a plant, in particular in the case of an ethylene tetramerization reaction, is as follows: The, in this case all-liquid, oligomerization reactor c is fed, on the one hand, with a gaseous phase 3 composed essentially of recycled ethylene 6 and of fresh ethylene 1, this phase having been compressed by the compressor f before injection at the operating pressure of the reactor c, namely in this case 81 bar absolute. The fresh ethylene of stream 1 before compression by the compressor f is at a pressure of a few tens of bar absolute, and the ethylene 6 is at a pressure of 11 bar absolute.

The reactor c is fed, on the other hand, with liquid phase, independently of the gaseous phase, this liquid phase consisting of stream 4 of solvent recycled through the pump g, the delivery pressure of which is 85 bar absolute. The operating temperature in the reactor c is here, for example, equal to 45° C. The column d and the section e are diagrammatic of a fractionation scheme which may be complex, as mentioned above. Notably, this scheme does not show the device for separating the neutralized catalyst from the reaction products and the solvent. The column d and the section e shown make it possible, on the one hand, to isolate the reaction products 8 and 9 and, on the other hand, to recycle the unconverted ethylene (stream 6) and the solvent (stream 4).

The principle of the reaction is that the gaseous ethylene is absorbed in the liquid phase and, placed in contact with the catalyst, is converted into reaction products before reaching the gaseous headspace.

It proves to be the case that, gradually, deposits of fouling solid of polymeric type are deposited on the surface of the reaction section, on the walls of the reactor but also in the recirculation loop containing the exchangers. As the reaction proceeds, the deposits become thicker and, when a maximum thickness is reached at the exchangers, production must be halted and the exchangers must be cleaned, in particular by emptying the recirculation loop and circulating therethrough a fluid which is sufficiently hot to dissolve these deposits. In the case, in particular, of two recirculation loops that can be switched over, it is possible to avoid halting production, but it is necessary to switch over between the two loops and clean them. This is a real difficulty since, on the industrial scale, this cleaning of the exchangers needs to be done very regularly, at time intervals often amounting to hours.

The invention consists in adding into the reaction section, in this case into the reactor c, packings, not to facilitate the exchange between gas phase and liquid phase, and even more so when the reactor is a single-phase reactor, but rather to better distribute the fouling deposits by favoring these deposits in the reactor on these additional contact surfaces. The thickening of the deposits on the exchangers is slowed down, and it is then possible to either space out production stoppages when the reactor only comprises a single recirculation loop with exchangers or when the cooling is performed by a jacketed reactor, or space out the switch-overs between the two recirculation loops when the loops are split into two as described in the above-mentioned patent.

The various types of packing which are suitable for the invention are described below in non-limiting fashion: it is possible in fact to envisage any internal that makes it possible to increase the surface area inside a chamber or a pipe in the case where there is provision to add packings in the recirculation loop(s) associated with the reactor c. The terms "packing" and "internal" are used without distinction in the present text to denote any component which is introduced into the reaction section, into the reactor and/or into the pipes under consideration in order to increase the contact surface area therein with the reaction medium and which is inert with respect to the reaction envisaged. The material of these packings may for example be made of a mineral material of the glass, ceramic or metal type, or of a polymer designed to resist the temperature and the compounds of the reaction medium, or any other material which is inert with respect to the reaction envisaged.

Figure 2:
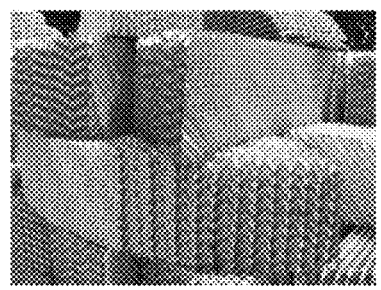
FIG. 2 represents an example of packing for a reactor of an oligomerization plant according to the invention.

As represented in FIG. 2, this may involve a packing of structured type, with a packing exhibiting two- or three-dimensional networks, which can be stacked on top of/alongside one another in a relatively compact manner.

Figure 3:
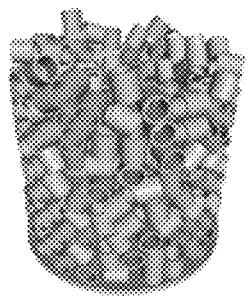
FIG. 3 represents another example of packing for a reactor of an oligomerization plant according to the invention.

As represented in FIG. 3, this may also involve random packing, with unit elements, here small cylinders, which are stacked randomly in the reactor.

Figure 4:
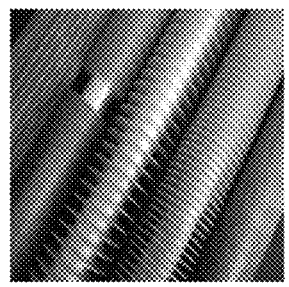
FIG. 4 represents another example of packing for a reactor of an oligomerization plant according to the invention.
Figure 5:
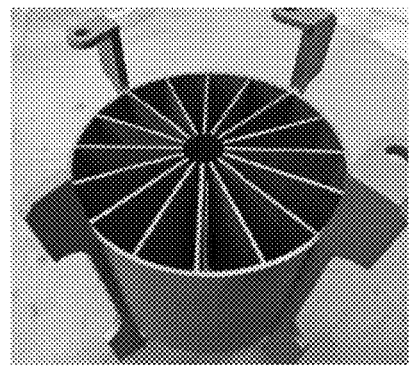
FIG. 5 represents another example of packing for a reactor of an oligomerization plant according to the invention.

As represented in FIGS. 4 and 5, this may also involve packings which define fins, grids, spirals, tubes or any other geometric shape that increases surface area per unit volume. In FIG. 4, these are solid cylindrical tubular elements comprising spiral fins on the external part. In FIG. 5, these are flat fins placed on a cylinder having a diameter of less than but close to that of the reaction chamber, having a length close to but less than that of the cylindrical portion of the reactor. Advantageously, these elements are disposed/oriented in the reactor (when they are disposed in the reactor) so as to minimize any hindrance caused by them to the passage of fluids from the inlets 3 and 4 of the reactor towards the outlet 5 thereof.

The surface area developed by packing may be from 10 to 200 $m^2/m^3$ for random-type packing; structured-type packing may achieve 200 $m^2/m^3$ or more.

The packing may be randomly deposited in the body of the reactor (with grills above and below which prevent it from being carried along into the rest of the plant), or else in the form of "slabs" dimensioned to the diameter of the reactor and placed one on top of the other. In this case, there may also be provision, if necessary, of mechanical reinforcement beams and/or grids.

Lastly, it can be envisaged to have other internals added as desired, which would make it possible to create surface area while meeting certain constraints specific to the process such as, in particular, a given spacing between two packing surfaces, a preferential passage direction, the need to avoid zones without fluid circulation, etc.

EXAMPLES 1 TO 4: TETRAMERIZATION OF ETHYLENE

Example 1 (Comparative)

This example implements the process as represented in FIG. 1, with the operating conditions described above for the tetramerization of ethylene, to obtain mainly 1-octene and possibly also 1-hexene.

The selectivity of the ethylene conversion reaction is such that 3000 ppm of fouling solid is produced for each kilogram of reactant converted. The production of the recovered product requires the conversion of 4600 kg/h of reactant, diluted in solvent.

The fouling solid is produced at the pace of the conversion of the reactant, thus 13.8 kg/h is produced. As the density of the solid is 900 $kg/m^3$, 0.0153 $m^3/h$ thereof is produced, which is distributed uniformly over all of the surfaces of the reaction section of the process.

Since this reaction is exothermic, the heat of the reaction is removed at heat exchangers placed on a recirculation loop external to the reactor, having a total surface area of 1400 $m^2$. The total reaction volume of 72 $m^3$ is distributed between the volume taken up by the heat exchangers and their recirculation loop, and a reaction chamber, i.e. the reactor. The total reaction volume is broken down in the following manner: 17 $m^3$ for the heat exchange loop, and 55 $m^3$ for the reactor.

Since the deposit of fouling solid inhibits the removal of heat at the exchanger, the efficiency of the exchangers is no longer satisfactory when the layer of solid reaches a thickness of 3 mm. The unit must then be cleaned.

The total surface area of the exchange loops is 1600 $m^2$, and that of the reactor is 130 $m^2$. The solid deposit therefore increases by $8.86 \times 10^{-6}$ m/h and reaches the maximum acceptable thickness of 3 mm in 338 hours, or approximately 14.1 days.

Example 2 (According to the Invention)

Example 1 is reproduced, with the difference that random-type packings are added (in this case, by way of example, metal rings as shown in FIG. 3, with an external diameter of 50 mm, a height of 50 mm and a thickness of 0.5 mm) into the reactor. These packings provide an additional surface area of 100 $m^2/m^3$, which is added to 80% of the liquid volume of the reactor. The surface area of the exchange loop is still 1600 $m^2$, whereas the surface area of the reactor with added surface area-creating internals is now 4530 $m^2$. This time, the solid deposit increases by $2.50 \times 10^{-6}$ m/h and reaches the maximum acceptable thickness of 3 mm in 1200 hours, or approximately 50.0 days.

With these packings, it was therefore possible to multiply the usage time of the unit before cleaning by a factor of 3.5, which is very significant.

Example 3 (Comparative)

This time, a jacketed reactor is chosen, which replaces the recirculation loop(s) equipped with exchangers of the previous examples.

An exothermic reaction takes place in this reactor, producing a fouling solid as by-product. The selectivity of the reaction is such that 3000 ppm of fouling solid is produced for each kilogram of reactant converted. The production of the recovered product requires the conversion of 4600 kg/h of reactant, diluted in solvent, in a reaction chamber of 55 m³ in total, which only corresponds to the internal volume defined by the reactor here.

The fouling solid is produced at the pace of the conversion of the reactant, thus 13.8 kg/h is produced. As the density of the solid is 900 kg/m³, 0.0153 m³/h thereof is produced, which is distributed uniformly over all of the surfaces of the reaction section of the process.

The heat of the reaction is removed at the walls of the jacket of the reactor, with a total surface area of 130 m². The surface area on which the solid is deposited is that of the reactor, i.e. 130 m². The solid deposit therefore increases by $1.18 \times 10^{-4}$ m/h and reaches the maximum acceptable thickness in 25.4 hours, or 1.06 days.

Example 4 (According to the Invention)

Example 3 is reproduced, with the difference that packings are added to the reactor: an additional surface area of 100 m²/m³ is added to 80% of the liquid volume of the reactor. The surface area of the reactor is still 130 m², while the surface area of the internals is 4400 m². This time, the fouling deposit increases by $3.38 \times 10^{-6}$ m/h and reaches the maximum acceptable thickness of 3 mm in 886 hours, or approximately 36.9 days.

The invention thus made it possible in this example to multiply the usage time of the unit before cleaning by a factor of 35.

Examples 5 to 8: Dimerization of Ethylene

Figure 6:
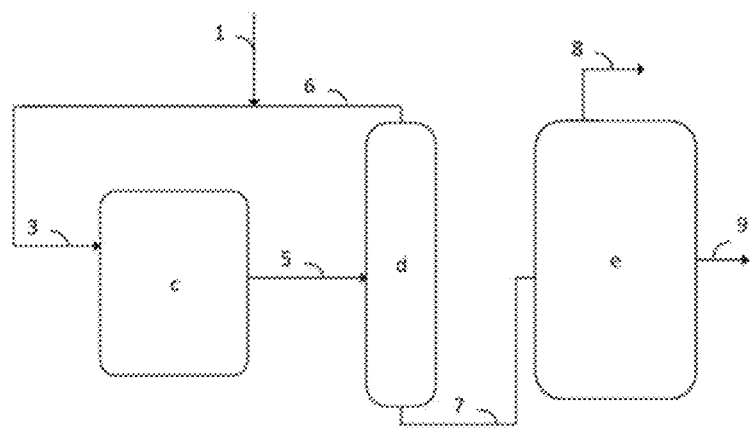
FIG. 6 is a variant of the diagram of an oligomerization plant of FIG. 1 designed for the dimerization of ethylene and capable of implementing the invention.

This second series of examples implements the process adapted with respect to that represented in FIG. 1, and implemented in the plant of FIG. 6, with operating conditions that have been modified with respect to the preceding examples in order this time to carry out a dimerization of ethylene to produce 1-butene.

A comparison of FIGS. 1 and 6 shows that the dimerization process differs from the tetramerization process essentially in that:
there is no longer the solvent recycle loop 4 equipped with pump g (no longer any solvent),
and there is no compressor f for compressing the stream obtained from streams 1 and The principle of the reaction is that the gaseous ethylene is absorbed in the liquid phase and, placed in contact with the catalyst, is converted into reaction products before reaching the gaseous headspace.

The operation of such a plant, in the case of an ethylene dimerization reaction, is as follows: The, in this case gas/liquid, oligomerization reactor c is fed, on the one hand, with a gaseous phase 3 composed essentially of recycled ethylene 6 and of fresh ethylene 1, at the operating pressure of the reactor c, namely in this case 26 bar absolute. The fresh ethylene of stream 1 at a pressure of a few tens of bar absolute, and the ethylene 6 is at a pressure of 29 bar absolute.

The operating temperature in the reactor c is here, for example, equal to 50° C. The column d and the section e are diagrammatic of a fractionation scheme which may be complex, as mentioned above. Notably, this scheme does not show the device for separating the neutralized catalyst from the reaction products. The column d and the section e shown make it possible, on the one hand, to isolate the reaction products 8 and 9 and, on the other hand, to recycle the unconverted ethylene (stream 6).

Example 5 (Comparative)

This example implements the process as modified with respect to FIG. 1, with the operating conditions described above.

The selectivity of the ethylene conversion reaction is such that 300 ppm of fouling solid is produced for each kilogram of reactant converted. The production of the recovered product requires the conversion of 4000 kg/h of reactant.

The fouling solid is produced at the pace of the conversion of the reactant, thus 1.20 kg/h is produced. As the density of the solid this time is 500 kg/m³, 0.0024 m³/h thereof is produced, which is distributed uniformly over all of the surfaces of the reaction section of the process.

Since this reaction is exothermic, the heat of the reaction is removed at heat exchangers placed on a recirculation loop external to the reactor, having a total surface area of 1000 m². The total reaction volume of 85 m³ is distributed between the volume taken up by the heat exchangers and their recirculation loop, and a reaction chamber, i.e. the reactor. The total reaction volume is broken down in the following manner: 25 m³ for the heat exchange loop, and 60 m³ for the reactor.

Since the deposit of fouling solid inhibits the removal of heat at the exchanger, the efficiency of the exchangers is no longer satisfactory when the layer of solid reaches a thickness of 1 mm. The unit must then be cleaned.

The total surface area of the exchange loops is 1200 m² (1000 for the exchangers and 200 for the lines), and that of the reactor is 78 m². The solid deposit therefore increases by $1.88 \times 10^{-6}$ m/h and reaches the maximum acceptable thickness of 1 mm in 532 hours, or approximately 22.2 days.

Example 6 (According to the Invention)

Example 5 is reproduced, with the difference that random-type packings are added (in this case, by way of example, metal rings as shown in FIG. 3, with an external diameter of 50 mm, a height of 50 mm and a thickness of 0.5 mm) into the reactor. These packings provide an additional surface area of 100 m²/m³, which is added to 80% of the liquid volume of the reactor. The surface area of the exchange loop is still 1200 m², whereas the surface area of the reactor with added surface area-creating internals is now 4878 m². This time, the solid deposit increases by $3.95 \times 10^{-7}$ m/h and reaches the maximum acceptable thickness of 1 mm in 2532 hours, or approximately 105.5 days.

With these packings, it was therefore possible to multiply the usage time of the unit before cleaning by a factor of 4.8, which is very significant.

Example 7 (Comparative)

This example implements the process as represented in FIG. 1, with the operating conditions modified with respect to the preceding examples for tetramerization that have already been specified above, in the following manner, to carry out this time a dimerization of ethylene to produce butenes or 1-butene, with the operating conditions for the dimerization described above for examples 5 and 6.

The selectivity of the ethylene conversion reaction is such that 100 ppm of fouling solid is produced for each kilogram of reactant converted. The production of the recovered product requires the conversion of 35 000 kg/h of reactant.

The fouling solid is produced at the pace of the conversion of the reactant, thus 3.5 kg/h is produced. As the density of the solid is 500 kg/m³, 0.007 m³/h thereof is produced, which is distributed uniformly over all of the surfaces of the reaction section of the process.

Since this reaction is exothermic, the heat of the reaction is removed at heat exchangers placed on a plurality of recirculation loops external to the reactor, having a total surface area of 7500 m². The total reaction volume of 323 m³ is distributed between the volume taken up by the heat exchangers and the recirculation loops, and a reaction chamber, i.e. the reactor. The total reaction volume is broken down in the following manner: 175 m³ for the heat exchange loops and 148 m³ for the reactor.

Since the deposit of fouling solid inhibits the removal of heat at the exchangers, the efficiency of the exchangers is no longer satisfactory when the layer of solid reaches a thickness of 1 mm. The unit must then be cleaned.

The total surface area of the exchange loops is 7500 m² (7000 for the exchangers and 500 for the lines), and that of the reactor is 141 m². The solid deposit therefore increases by $9.16 \times 10^{-7}$ m/h and reaches the maximum acceptable thickness of 1 mm in 1092 hours, or approximately 45.5 days.

Example 8 (According to the Invention)

Example 7 is reproduced, with the difference that random-type packings are added (in this case, by way of example, metal rings as shown in FIG. 3, with an external diameter of 50 mm, a height of 50 mm and a thickness of 0.5 mm) into the reactor. These packings provide an additional surface area of 100 m²/m³, which is added to 80% of the liquid volume of the reactor. The surface area of the exchange loop is still 7500 m², whereas the surface area of the reactor with added surface area-creating internals is now 11981 m². This time, the solid deposit increases by $3.60 \times 10^{-7}$ m/h and reaches the maximum acceptable thickness of 1 mm in 2783 hours, or approximately 116.0 days.

With these packings, it was therefore possible to multiply the usage time of the unit before cleaning by a factor of 2.55, which is very significant.

It has thus been verified that the addition of packing makes it possible to at least double, or even at least triple, the operating time of the plant before stoppage for cleaning the heat exchangers. This is a considerable gain in terms of productivity which, in addition, does not disturb the operation of the plant nor the yield or the quality of the alpha-olefins thus produced, and which could thus be demonstrated, irrespective of whether the reaction involved is a dimerization or a tetramerization of ethylene.

The invention claimed is:

1. A plant for oligomerizing C2 to C4 olefins to produce oligomerized alpha-olefins, with production of a fouling by-product in the form of a deposit, said plant comprising a reaction section comprising:
   a reactor for two-phase gas/liquid or single-phase all-liquid oligomerization of C2 to C4 olefins in the presence of a homogeneous oligomerization catalyst and an optional solvent, and
   cooling means associated with said reactor in the form of at least one cooling circuit external to the reactor and/or in the form of a jacket of the walls of the reactor,
   wherein packings are disposed in the reaction section in order to increase the contact surface area per unit volume that is accessible to the deposition of the fouling by-product.

2. The plant as claimed in claim 1, wherein the cooling means are at least one cooling circuit external to the reactor, and in that the packings are disposed in the reactor only.

3. The plant as claimed in claim 1, wherein the packings are disposed in a liquid-filled volume VI of the reactor.

4. The plant as claimed in claim 1, wherein the packings are selected from one at least of the following packings: structured packing, random packing, and internals defining fins.

5. The plant as claimed in claim 1, wherein the external cooling circuit comprises a recirculation loop for the liquid phase of the reactor, said loop incorporating one or more heat exchangers.

6. The plant as claimed in claim 1, wherein the external cooling circuit comprises at least two separate recirculation loops each incorporating one or more heat exchangers, and which are operational in alternation.

7. The plant as claimed in claim 1, further comprising a separation section for separating reaction effluents resulting from the reaction section, downstream of the oligomerization reactor, said separation section comprising at least a first fractionating column for fractionating said reaction effluents so as to obtain a fraction containing the olefin(s), and at least one bottom fraction.

8. The plant as claimed in claim 7, wherein a solvent is used and the separation section comprises, downstream of the first fractionating column, a distillation fractionation section for fractionating by distillation so as to obtain at least one fraction enriched in alpha-olefin oligomerization products and one fraction enriched in solvent.

9. The plant as claimed in claim 7, wherein a solvent is used and the plant further comprises a loop (4) for recycling the solvent from the separation section to the reaction section.

10. The plant as claimed in claim 7, further comprising a loop (6) for recycling olefin(s) from the separation section to the reaction section.

11. The process as claimed in claim 1, wherein the external cooling circuit of the reactor comprises at least two separate recirculation loops each incorporating one or more heat exchangers, which are operational in alternation, and in that at least one of the recirculation loops is operational while the exchangers of the other recirculation loop(s) which are not operational are being cleaned.

12. The plant as claimed in claim 1, wherein the cooling means are at least one cooling circuit external to the reactor, and in that the packings are disposed in the reactor and in the cooling circuit(s).

13. The plant as claimed in claim 1, wherein the cooling means are at least one cooling circuit external to the reactor, and in that the packings are disposed in the cooling circuit(s) only.

14. The plant as claimed in claim 1, wherein the packings are disposed in at least 5% of a liquid-filled volume VI of the reactor.

15. The plant as claimed in claim 1, wherein the packings are disposed in between 30 and 90% of a liquid-filled volume VI of the reactor.

16. The process as claimed in claim 11, wherein the recirculation loop(s) being cleaned are leaned with the aid of a fluid the temperature of which is greater than the dissolution temperature of the fouling by-product.

17. A process for oligomerizing C2-C4 starting olefins to produce oligomerized alpha-olefins, comprising oligomerizing C2-C4 starting olefins in the presence of an oligomerization catalyst and, optionally, a solvent, wherein oligomerizing said C2-C4 starting olefins results in production of a solid fouling by-product,
   wherein the oligomerization is performed in a reaction section comprising:

a reactor (c) for two-phase gas/liquid or single-phase, and cooling means associated with said reactor in the form of at least one cooling circuit external to the reactor and/or in the form of a jacket of the walls of the reactor, wherein the contact surface area per unit volume of the reaction section which is available for the deposition of the fouling by-product is increased by disposing packings in the reactor.

18. The process as claimed in claim 17, wherein the contact surface area per unit volume of the reaction section is increased by virtue of the presence of the packings in the reaction section by at least 5 $m^2/m^3$.

19. The process as claimed in claim 17, wherein the oligomerization involves dimerization, trimerization or tetramerization of ethylene.

20. The process as claimed in claim 17, wherein the contact surface area per unit volume of the reaction section is increased by virtue of the presence of the packings in the reaction section by at least 10 $m^2/m^3$.

21. The process as claimed in claim 17, wherein the contact surface area per unit volume of the reaction section is increased by virtue of the presence of the packings in the reaction section by between 10 and 500 $m^2/m^3$.

* * * * *